United States Patent [19]
Tirelli et al.

[11] Patent Number: 4,989,227
[45] Date of Patent: Jan. 29, 1991

[54] CASSETTE CARRIER ADAPTABLE IN SIZE AND POSITION FOR MAMMOGRAPHY

[75] Inventors: Marco Tirelli, Palaiseau; Didier Rouchy, Les Clayes Sous Bois; Jean-Claude Rapeau, Velizy Villacoublay, all of France

[73] Assignee: General Electric CGR S.A., Issy les Molineaux, France

[21] Appl. No.: 497,709

[22] Filed: Mar. 23, 1990

[30] Foreign Application Priority Data
Apr. 28, 1989 [FR] France ................... 89 05666

[51] Int. Cl.⁵ .......................................... G03B 42/02
[52] U.S. Cl. ....................................... 378/177; 378/181
[58] Field of Search .............................. 378/177, 181

[56] References Cited
U.S. PATENT DOCUMENTS
4,357,538 11/1982 Hunt et al. ................... 378/175

FOREIGN PATENT DOCUMENTS
2196088 of 0000 France.

Primary Examiner—Craig E. Church
Attorney, Agent, or Firm—Walter C. Farley

[57] ABSTRACT

The invention relates to mammographs, and more particularly to a device enabling the mammograph to adapt to different sizes of a cassette, and to displace cassettes. The device essentially comprises a sliding member which, when moved, changes the distance between holding pegs to match new lateral dimensions of a the cassette while still pressing the cassette against a reference edge of the table. In addition, the sliding member is carried on a plate member which moves in such a manner that one or other of the side edges of the cassette can be brought into alignment with the corresponding side of the table.

4 Claims, 4 Drawing Sheets

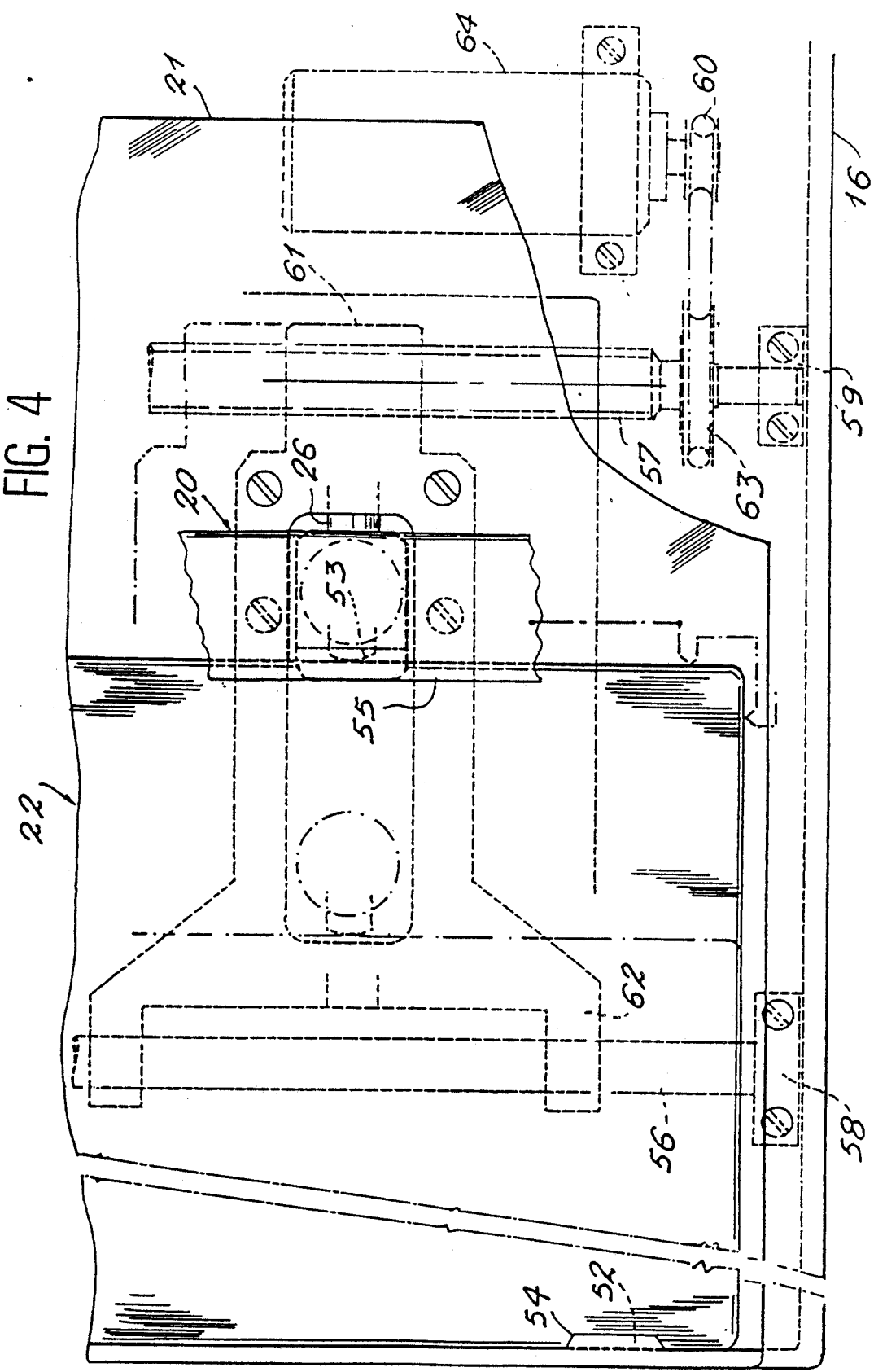

CASSETTE CARRIER ADAPTABLE IN SIZE AND POSITION FOR MAMMOGRAPHY

BACKGROUND OF THE INVENTION

The invention relates to mammography apparatus, and more particularly to devices within such apparatuses for supporting a cassette containing the sensitive film.

As shown in FIG. 1, mammographic type X-ray systems comprise a source 10 of X-radiation carried by a bracket 11 disposed at the top of a vertical plate 12. The vertical plate includes an assembly 13 on which the breast 16 to be examined is placed resting directly on a horizontal panel 15. The breast is compressed by a pad 17 which is transparent to X-rays and vertically moveable along the vertical plate 12.

In order to adapt to the height of the patient, the vertical plate 12 is mounted on a vertical column 9 standing on the ground and it moves vertically along said column by means of an appropriate mechanism.

The top of the assembly 13 immediately beneath the panel 15 has a tunnel in which a device is housed for receiving a cassette 18. The cassette is constituted by a black box enclosing at least one film 14 which is sensitive to direct X radiation or to photon radiation emitted by a screen (not shown) which itself receives the X radiation. The latent image of the breast appears on this film after an appropriate exposure time. When the film is developed, it constitutes an X-ray picture.

The device containing the cassette is called a cassette support and it is a removable element which is slid into the tunnel prior to taking the X-ray with the cassette inserted therein. The sensitive films come in standardized sizes, e.g. 18 cm × 24 cm or 24 cm × 30 cm, and the same is true of cassettes which are intended to contain the films, and the same also applies to cassette support.

In order to change from a cassette of given dimensions to another of different dimensions, it is normally necessary to change the cassette support at the same time. A cassette support is thus generally provided matching the dimensions of the cassette and constituting a kind of adapter which is associated with each type of cassette. This gives rise to additional cost when it is desired to use a mammograph for all the usual sizes of cassette, and it also requires bulky items such as cassette supports to be handled during examination. These drawbacks are even more pronounced when the cassette support includes a moving anti-diffusion screen 19 disposed between the panel 15 and the cassette 18, thereby increasing cost and weight.

SUMMARY OF THE INVENTION

An object of the present invention is therefore to provide a cassette support which adapts to all sizes of cassette used in this field.

The advantage provided by the present invention is even more important when the cassette support further includes a moving anti-diffusion screen. In this case, the cassette support includes a mechanism for displacing the anti-diffusion screen and this increases its cost.

Thus, another object of the present invention is to provide a cassette support which requires only one mechanism to be used for displacing the anti-diffusion screen.

For any given mammograph, the horizontal panel 15 has outside dimensions adapted to the dimensions of the largest cassette with which it is intended to be used. When cassettes of smaller dimensions are used, they must be positioned inside the largest dimensions of the panel 15 so that the side of each cassette closest to the outside edge of the panel 15 (the reference side) is in alignment therewith. It is therefore necessary for the cassette support which is used to be adapted to the desired position, which is why there are as many cassette supports as there are different sizes of cassette.

Another object of the present invention is therefore to provide a cassette carrier enabling the position of the cassette relative to the position of the panel to be changed while still retaining the reference side.

The present invention provides a cassette carrier for supporting a cassette on a table, the cassette containing at least one sensitive film, and the cassette carrier comprising:

a plate member which is mounted to move relative to the table in a first direction by virtue of a first displacement mechanism;

a slide member which is mounted to move relative to the plate member by virtue of a second displacement mechanism and in a second direction perpendicular to the first; and means associated with the slide member for holding the cassette in position relative to the plate member and for adapting to the dimensions of the cassette, Wherein said first displacement mechanism comprises at least two guides slidably supporting tabs integral with the plate member, one of the guides being threaded and co-operating with a drive nut in such a manner that rotation of the threaded guide causes the plate member to be displaced in a desired direction, the other guide being smooth.

The second displacement mechanism comprises at least one guide integral with the plate member and disposed perpendicularly to the guides of the first displacement mechanism and on which the slide member slides so as to take up at least two positions each corresponding to a locking groove carried by said guide and co-operating with locking/unlocking means carried by the slide member.

The means associated with the slide member for holding the cassette comprise two holding pegs carried by respective arms supported by the slide member and grasping two of the four corners of the cassette, each of said arms including a pin which co-operates with a first slot formed in the sliding member and with a second slot formed in the plate member such that displacement of the sliding member changes the distance between the holdings pegs in order to adapt to the dimensions of the cassette.

BRIEF DESCRIPTION OF THE DRAWINGS

Other characteristics and advantages of the present invention will appear from reading the following description of a particular embodiment, said description being made with reference to the accompanying drawings, in which:

FIG. 4 is a plan view showing the mechanism for displacing the cassette laterally;

BRIEF DESCRIPTION OF A PREFERRED EMBODIMENT

Figure 1:
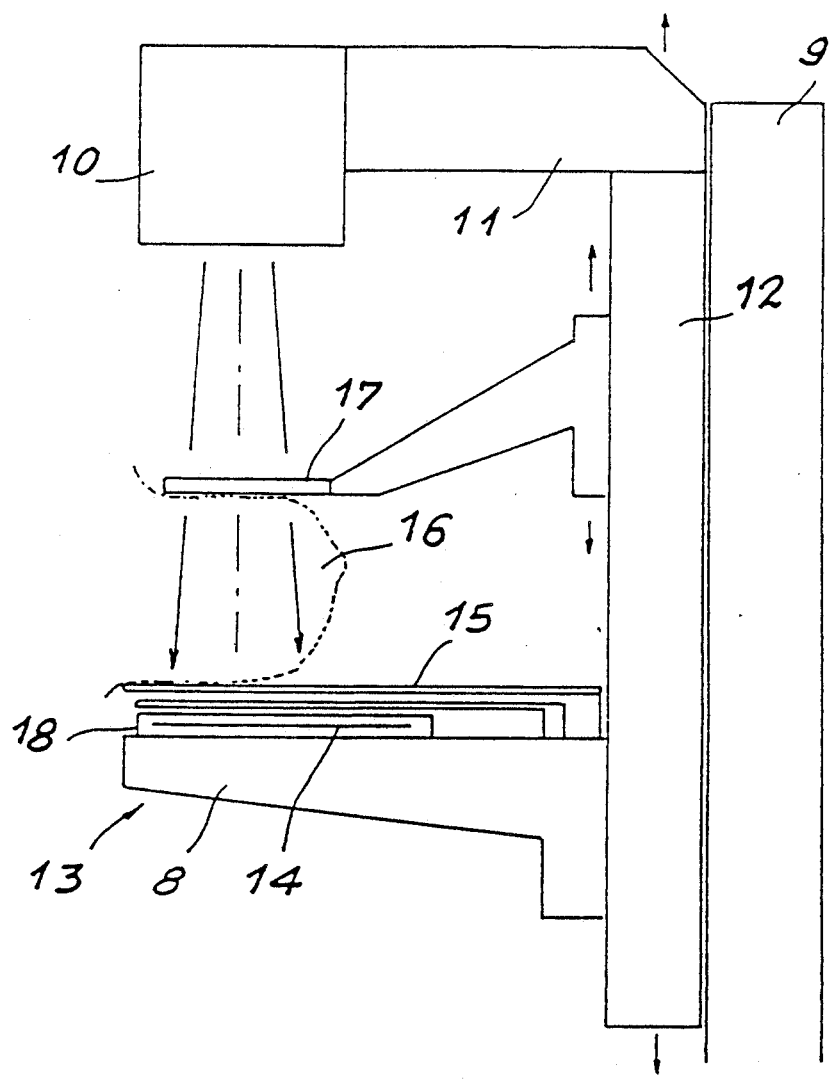
FIG. 1 is a diagrammatic section view of a mammograph.

The invention is described in its application to a cassette carrier adaptable to two sizes of cassette, e g the 24 cm ×30 cm size and the 18 cm ×24 cm size.

In the figures, reference 8 designates the table on which the cassette carrier of the invention is placed. The cassette carrier essentially comprises a sliding member 20 which carries holding pegs 23 and 24 for holding a cassette 18, a plate member 21 which supports the sliding member 20, and a plate member displacement mechanism 22. The sliding member 20 is constituted by a part 25 which slides on a guide 26 along the directions indicated by arrows 27 and 28. The guide 26 is fixed to the plate member 21 by tabs 29 and 30 and by screws 31 and 32 for fixing the tabs to the plate member and a screw 33 for fixing the guide within the tabs. The guide 26 includes two grooves 35 and 34 each corresponding to a position of the sliding member 20 on the guide 26. These grooves co-operate with a locking pin 36 carried by the sliding member 20, said locking pin being held in the grooves 34 and 35 by a spring 37. A button 38 serves to unlock the pin and displace the sliding member from one groove to the other.

The sliding member 20 has two ends 39 and 40 each carrying a respective arm 41 and 42 for holding corresponding corners of the cassette 18 by means of the holdings pegs 23 and 24. A pin 45 or 46 is carried by the end of each arm 41 or 42 opposite to the end carrying the holding peg. The pin 45 co-operates with two slots, one of the slots 47 is made in the sliding member parallel to the edge 51 of the cassette 18, and the other slot 49 is made in the platen in an oblique direction relative to the edge 51. Similarly, the pin 46 co-operates with two slots: one of the slots, 48, being made in the sliding member parallel to the edge 51 of the cassette 18, and the other slot, 50, being made in the plate member along a direction oblique to the said edge 51.

Figure 2:
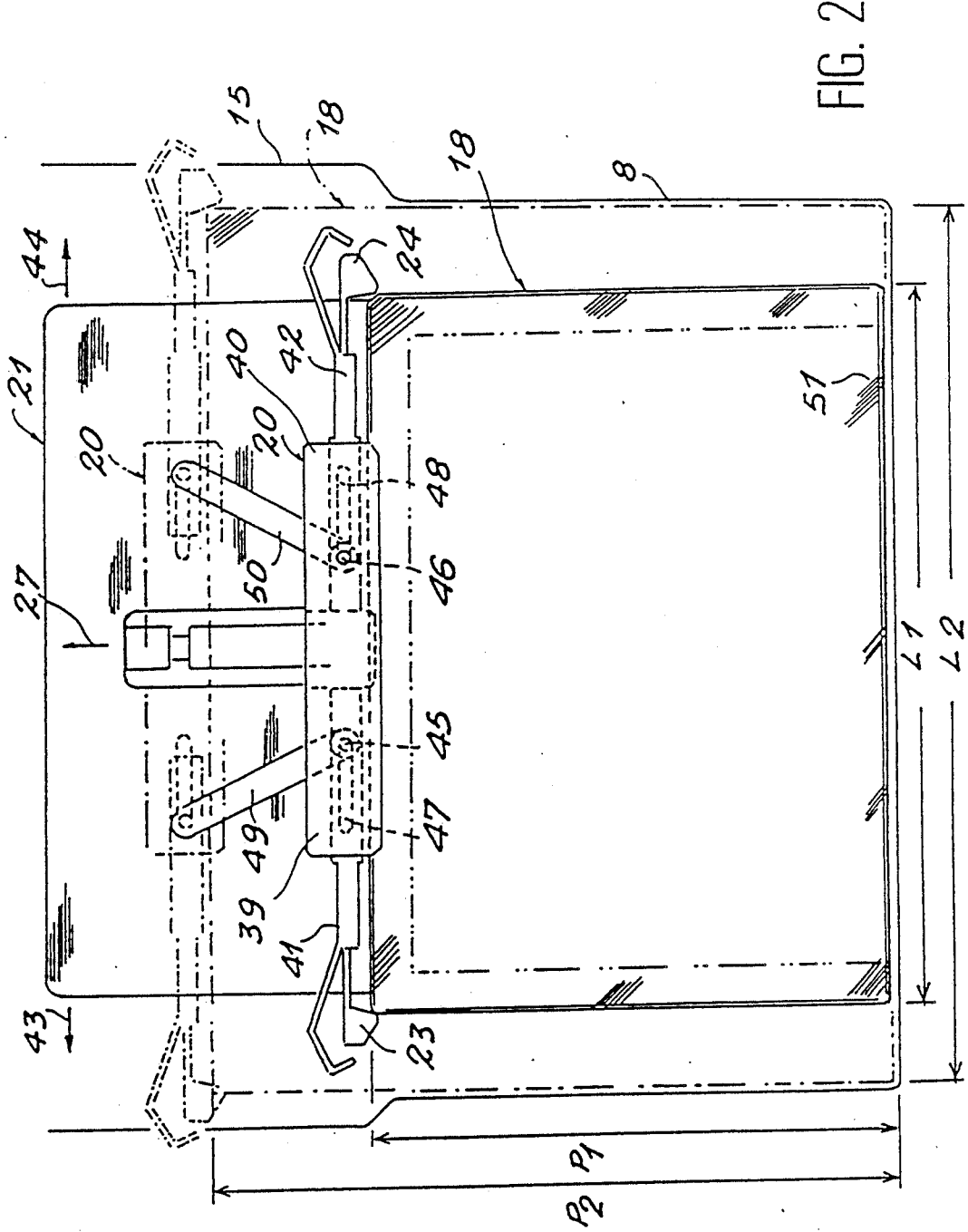
FIG. 2 is a plan view of the cassette carrier of the invention, with the anti-diffusion screen and the panel taken away.

It will easily be understood, with reference to FIG. 2, that this assembly ensures that moving the sliding member along arrow 27 moves the arms in the same direction, thereby changing from cassette width P1 to cassette width P2. Simultaneously, the holding pegs 23 and 24 move apart from one another so as to change from cassette length L1 to cassette length L2. The device is thus capable of adapting to two sizes of cassette: L1×P1 and L2×P2.

In order to hold the cassette 18 firmly in place on the plate member 21, the latter includes an abutment 52 which bears against the side 51 of the cassette opposite to its side adjacent to the sliding member, with the cassette being pressed against the abutment 52 by a resilient pusher 53 provided inside the sliding member. In addition, in order to prevent the cassette escaping upwards, the abutment 52 and the sliding member 20 are provided with respective lips 54 and 55.

Figures 3, 6:
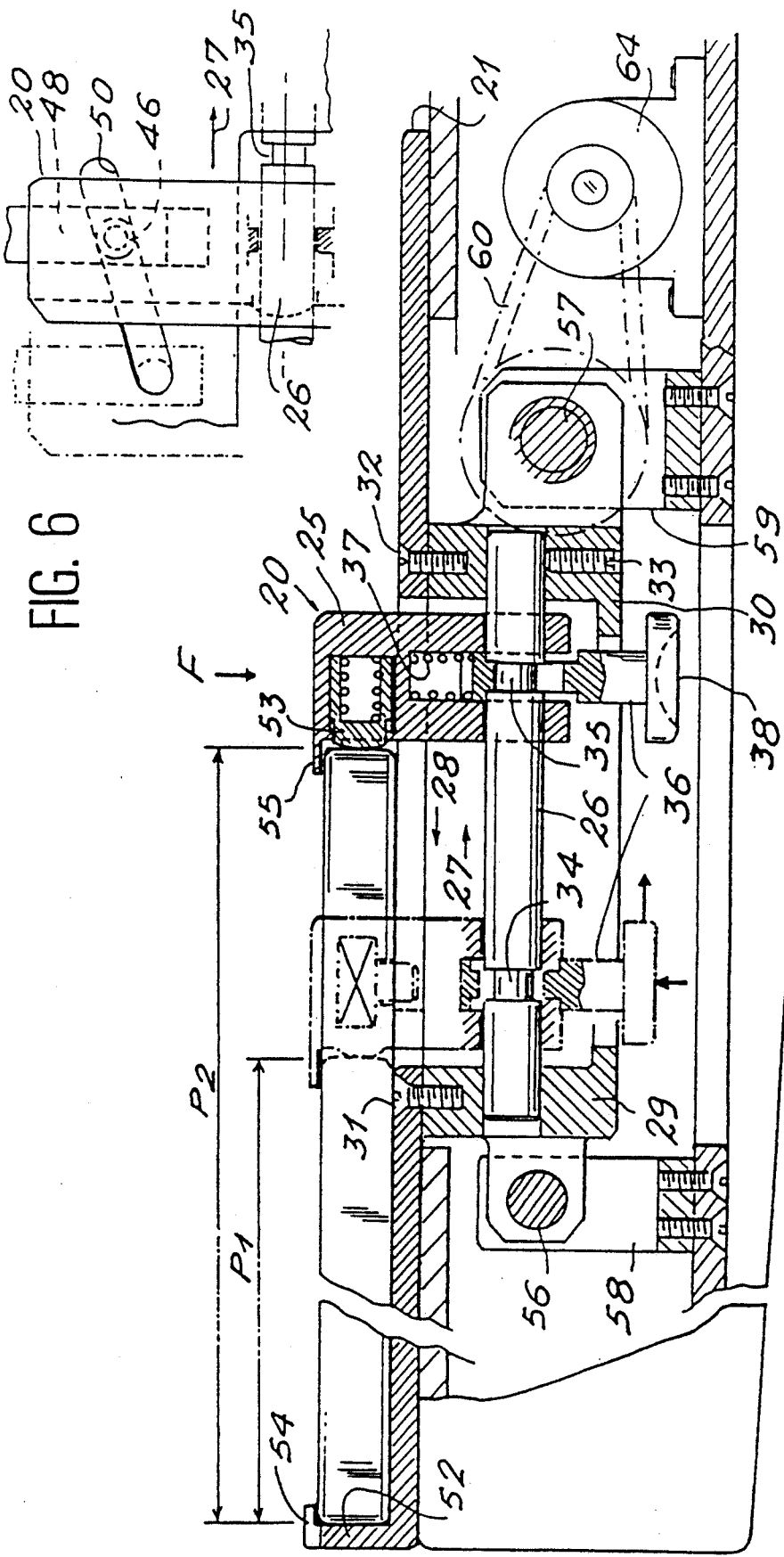
FIG. 3 is a diagrammatic vertical section view of the cassette carrier of the invention.
FIG. 6 is an explanatory view showing a portion of the apparatus seen along arrow F of FIG. 3.

In order to displace the cassette 18 in the direction of arrow 43 or 44, the invention proposes a plate member displacement mechanism. This mechanism is constituted by the tabs 29 and 30 (FIG. 3) with the tab 29 co-operating with a smooth guide 56 and the tab 30 co-operating with a threaded guide 57, and with each of the guides being fixed to the table 8 by a corresponding support 58 or 59 and screws 65 and 66. The tab 29 slides on the smooth guide 56 via a fork 62 while the tab 30 includes a tapped bore or drive nut 61 which co-operates with the threaded guide 57. The guide 56 is fixed, whereas the guide 57 rotates in support bearings 59. The guide 57 is rotated by a pulley 63 fixed to the guide 57 and driven, for example, by a motor 64 by means of a belt 60. By rotating the threaded guide 57, the nut 61 is displaced in the desired direction, thereby displacing the platen 21 and the cassette supported thereby.

Figure 5A:
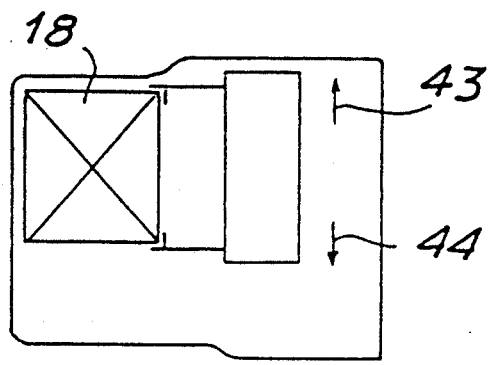
FIGS. 5a and 5b show two positions of the cassette which can be obtained by the cassette carrier of the invention.

FIG. 5a shows one of the extreme positions that a small L1×P1 sized cassette can take up when the plate member displacement mechanism is displaced in the direction of arrow 43.

Figure 5B:
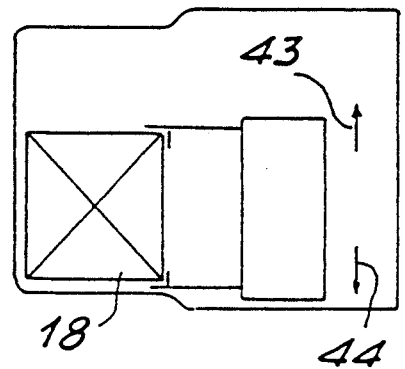

FIG. 5b shows the other extreme position which a small L1×P1 sized cassette can take up when the plate member displacement mechanism is displaced in the direction of arrow 44.

What is claimed is:

1. A cassette carrier for supporting a cassette on a table, the cassette containing at least one sensitive film, and the cassette carrier comprising :

a plate member which is mounted to move relative to the table in a first direction by virtue of a first displacement mechanism;

a sliding member which is mounted to move relative to the plate member by virtue of a second displacement mechanism and in a second direction perpendicular to the first; and means associated with the sliding member holding the cassette in position relative to the plate member and for adapting to the dimensions of the cassette, Wherein said first displacement mechanism comprises at least two guides slidably supporting tabs integral with the plate member, one of the guides being threaded and co- operating with a drive nut in such a manner that rotation of the threaded guide causes the plate member to be displaced in a desired direction, the second guide being smooth.

2. A cassette carrier according to claim wherein said first displacement mechanism further includes a motor which rotates said threaded guide.

3. A cassette carrier according to claim 1, wherein said second displacement mechanism comprises at least one guide integral with the plate member and disposed perpendicularly to the guides of the first displacement mechanism and on which the sliding member slides so as to take up at least two positions each corresponding to a locking groove carried by said guide and co-operating with locking/unlocking means carried by the sliding member.

4. A cassette carrier according to claim I, wherein said means associated with the sliding member for holding the cassette comprise two holding pegs carried by respective arms (41, 42) carried by the sliding member and grasping two of the four corners of the cassette, each of said arms including a pin which co-operates each with a first slot formed in the sliding member and with a second slot formed in the sliding member such that displacement of the sliding member changes the distance between the holding pegs in order to adapt to the dimensions of the cassette.

* * * * *